United States Patent
Sans et al.

(10) Patent No.: US 8,178,481 B2
(45) Date of Patent: May 15, 2012

(54) CLEAR CLEANSING COMPOSITION

(75) Inventors: Anne Sans, Amfreville sur Iton (FR); Laurent Helan, Alizay (FR); Marilyne Candolives, Princeton, NJ (US)

(73) Assignee: Johnson & Johnson Consumer Holdings France (FR)

( * ) Notice: Subject to any disclaimer, the term of this patent is extended or adjusted under 35 U.S.C. 154(b) by 65 days.

(21) Appl. No.: 12/293,690

(22) PCT Filed: Mar. 20, 2007

(86) PCT No.: PCT/EP2007/002438
§ 371 (c)(1),
(2), (4) Date: Jun. 23, 2010

(87) PCT Pub. No.: WO2007/112852
PCT Pub. Date: Oct. 11, 2007

(65) Prior Publication Data
US 2010/0267598 A1    Oct. 21, 2010

(30) Foreign Application Priority Data

Mar. 31, 2006    (EP) .................................... 06290543

(51) Int. Cl.
*A61K 7/50*    (2006.01)
(52) U.S. Cl. ........ 510/130; 510/156; 510/424; 510/426; 510/490; 510/505

(58) Field of Classification Search ........................ None
See application file for complete search history.

(56) References Cited

U.S. PATENT DOCUMENTS

| 5,030,374 A | 7/1991 | Tranner |
| 5,888,951 A * | 3/1999 | Gagnebien et al. ........... 510/130 |
| 2002/0039976 A1 | 4/2002 | Sebillotte |

FOREIGN PATENT DOCUMENTS

| DE | 198 13 057 A1 | 9/1999 |
| EP | 0 569 028 A | 11/1993 |
| EP | 1 180 363 A | 2/2002 |
| EP | 1 100 459 | 10/2003 |
| WO | WO 03/051319 A | 6/2003 |
| WO | 2004/058212 | 7/2004 |
| WO | 2004/100862 | 11/2004 |

OTHER PUBLICATIONS

Happi Household and Personal Products Industry, Rodman Publishing, Ramsey, NJ, Jul. 1999, p. 16 XP002136053—Clear, mild shower gel.

* cited by examiner

*Primary Examiner* — Necholus Ogden, Jr.

(57) ABSTRACT

A clear cleansing composition that also provides excellent moisturization is described. The composition comprises about 0.05 to about 30 weight percent anionic surfactant, an additional surfactant selected from about 0.5 to about 20 weight percent amphoteric surfactant, about 0.1 to about 20 weight percent nonionic surfactant, or both, and about 0.1 to about 50 weight percent humectant. Advantageously, the composition is also mild.

2 Claims, No Drawings

CLEAR CLEANSING COMPOSITION

The present invention relates to a clear cleansing composition that provides excellent moisturization. The composition is also advantageously mild and delivers good foaming and sensory benefits like skin softness. The composition comprises an anionic surfactant, an additional surfactant that is an amphoteric surfactant, a nonionic surfactant, or a mixture of the two, and a humectant.

BACKGROUND OF THE INVENTION

A clear and transparent appearance in personal care and cosmetic products has become an important product feature as the consumer associates it with attributes such as pureness, mildness, cleanliness, freshness, lightness and often possessing cooling properties. Clear products are used for a variety of adult and baby applications. Another benefit of a clear appearance, in combination with transparent packaging, is that the consumer is readily able to view and inspect the product.

Clear oil-in-water emulsions containing silicone oils are disclosed in WO2004/100862 and WO2004/058212. EP 1 100 459 B1 discloses a clear, single phase composition containing surfactants and an oil component. U.S. Pat. No. 5,030,374 discloses a clear, non-foaming gel facial cleanser consisting essentially of mild nonionic detergent and wound cleanser, moisturizer/humectant, moisturizer/emollient, viscosity stabilizer, pH adjuster, substantive emollient, preservative/bacterial inhibitor, solubilizer, masking agent, and deionized water.

It would de desirable to have a cleansing composition that is clear, mild, foaming and capable of moisturization. Such a composition is disclosed herein.

SUMMARY OF THE INVENTION

The present invention provides a clear cleansing composition comprising about 0.05 to about 30 weight percent anionic surfactant, an additional surfactant selected from about 0.5 to about 20 weight percent amphoteric surfactant, about 0.1 to about 20 weight percent nonionic surfactant, or both, and about 0.1 to about 50 weight percent humectant, wherein said composition provides moisturization duration for at least about 4 hours.

DETAILED DESCRIPTION OF THE INVENTION

All weight percents are based on the total weight of the composition.

Anionic Surfactants

The clear cleansing composition comprises at least one anionic surfactant. Nonlimiting examples of anionic surfactants useful in the compositions of the present invention are disclosed in McCutcheon's, *Detergents and Emulsifiers*, North American edition (1986), published by Allured Publishing Corporation; McCutcheon's, *Functional Materials*, North American Edition (1992); and U.S. Pat. No. 3,929,678, to Laughlin et al., issued Dec. 30, 1975, each of which is incorporated by reference herein in their entirety.

A wide variety of anionic surfactants are potentially useful herein. Nonlimiting examples of anionic surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and combinations thereof. Combinations of anionic surfactants can be used effectively in the present invention.

Anionic surfactants for use in the composition include alkyl and alkyl ether sulfates. These materials have the respective formulae $R_1O—SO_3M$ and $R_1(CH_2H_4O)_x—O—SO_3M$, wherein $R_1$ is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Specific examples of alkyl sulfates, which may be used in the cleansing component are sodium, ammonium, potassium, magnesium, or TEA salts of lauryl or myristyl sulfate. Examples of alkyl ether sulfates, which may be used include ammonium, sodium, magnesium, or TEA laureth-3 sulfate.

Another suitable class of anionic surfactants are the sulfated monoglycerides of the form $R_1CO—O—CH_2—C(OH)H—CH_2—O—SO_3M$, wherein $R_1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R_1SO_3M$, wherein $R_1$ is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones, which have been formed in the reaction are hydrolyzed to give the corresponding hydroxyalkanesulfonate. An example of a sulfonated olefin is sodium C14/C16 alpha olefin sulfonate.

Other suitable anionic surfactants are the linear alkylbenzene sulfonates of the form $R_1—C_6H_4—SO_3M$, wherein $R_1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for the cleansing formulation include the primary or secondary alkane sulfonates of the form $R_1SO_3M$, wherein $R_1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method. The sulfonation can occur in either the secondary or primary positions of the alkyl chain. An example of an alkane sulfonate useful herein is alkali metal or ammonium C13-C17 paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; and dioctyl esters of sodium sulfosuccinic acid.

Also useful are taurates based on taurine, which is also known as 2-aminoethanesulfonic acid. Examples of taurates include N-alkyltaurines such as the one prepared by reacting dodecylamine with sodium isethionate as detailed in U.S. Pat. No. 2,658,072 which is incorporated herein by reference in its entirety. Other examples based of taurine include the acyl taurines formed by the reaction of n-methyl taurine with fatty acids (having from about 8 to about 24 carbon atoms).

Another class of anionic surfactants suitable for use in the cleansing formulation is the acyl isethionates. The acyl isethionates typically have the formula $R_1CO-O-CH_2CH_2SO_3M$ wherein $R_1$ is a saturated or unsaturated, branched or unbranched alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R_1-OCH_2-C(OH)H-CH_2-SO_3M$, wherein $R_1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form $R_1-CH(SO_4)-COOH$ and sulfonated methyl esters of the from $R_1-CH(SO_4)-CO-O-CH_3$, where $R_1$ is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic surfactants include phosphates such as monoalkyl, dialkyl, and trialkylphosphate salts formed by the reaction of phosphorous pentoxide with monohydric branched or unbranched alcohols having from about 8 to about 24 carbon atoms. These could also be formed by other known phosphation methods. An example from this class of surfactants is sodium mono or dilaurylphosphate.

Other anionic surfactants include acyl glutamates corresponding to the formula $R_1CO-N(COOH)-CH_2CH_2-CO_2M$ wherein $R_1$ is a saturated or unsaturated, branched or unbranched alkyl or alkenyl group of about 8 to about 24 carbon atoms, and M is a water-soluble cation. Nonlimiting examples include sodium lauroyl glutamate and sodium cocoyl glutamate.

Other anionic surfactants include alkanoyl sarcosinates corresponding to the formula $R_1CON(CH_3)-CH_2CH_2-CO_2M$ wherein $R_1$ is a saturated or unsaturated, branched or unbranched alkyl or alkenyl group of about 10 to about 20 carbon atoms, and M is a water-soluble cation. Nonlimiting examples include sodium lauroyl sarcosinate, sodium cocoyl sarcosinate, and ammonium lauroyl sarcosinate.

Other anionic surfactants include alkyl ether carboxylates corresponding to the formula $R_1-(OCH_2CH_2)_x-OCH_2-CO_2M$ wherein $R_1$ is a saturated or unsaturated, branched or unbranched alkyl or alkenyl group of about 8 to about 24 carbon atoms, x is 1 to 10, and M is a water-soluble cation. Nonlimiting examples include sodium laureth carboxylate.

Other anionic surfactants include acyl lactylates corresponding to the formula $R_1CO-[O-CH(CH_3)-CO]_x-CO_2M$ wherein $R_1$ is a saturated or unsaturated, branched or unbranched alkyl or alkenyl group of about 8 to about 24 carbon atoms, x is 3, and M is a water-soluble cation. Nonlimiting examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Other anionic surfactants include natural soaps derived from the saponification of vegetable and/or animal fats & oils examples of which include sodium laurate, sodium myristate, palmitate, stearate, tallowate, cocoate.

Any counter cation, M, can be used on the anionic surfactant. Preferably, the counter cation is selected from the group consisting of sodium, potassium, ammonium, monoethanolamine, diethanolamine, and triethanolamine. More preferably, the counter cation is ammonium.

Preferably, the anionic surfactant is selected from the group consisting of sodium lauryl ether sulfate, sodium lauroyl glutamate, and mixtures thereof.

The amount of anionic surfactant is in the range of about 0.05 to about 30 weight percent. Preferably, the amount of anionic surfactant is in the range of about 1 to about 10 weight percent.

Additional Surfactants

The composition also contains an additional surfactant that is an amphoteric surfactant, a nonionic surfactant, or a mixture of the two.

Nonionic Surfactants

Nonlimiting examples of nonionic surfactants are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g., C8-C30 alcohols, with sugars or starches or sugar or starch polymers, i.e., glycosides or polyglycosides. These compounds can be represented by the formula $(S)_n-O-R$ wherein S is a sugar moiety such as glucose, fructose, mannose, and galactose; n is an integer of from about 1 to about 1000, and R is a C8-C30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-C20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the formula:

wherein: $R^1$ is H, $C_1$-$C_4$ alkyl, 2-hydroxyethyl, 2-hydroxypropyl, preferably $C_1$-$C_4$ alkyl, more preferably methyl or ethyl, most preferably methyl; $R^2$ is $C_5$-$C_{31}$ alkyl or alkenyl, preferably $C_7$-$C_{19}$ alkyl or alkenyl, more preferably $C_9$-$C_{17}$ alkyl or alkenyl, most preferably $C_{11}$-$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060; U.S. Pat. No. 2,965,576, U.S. Pat. No. 2,703,798, and U.S. Pat. No. 1,985,424, each of which are incorporated herein by reference in their entirety.

Other examples of nonionic surfactants include amine oxides. Amine oxides correspond to the general formula $R_1R_2R_3N$—O, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyidi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

Nonlimiting examples of preferred nonionic surfactants for use herein are those selected form the group consisting of C8-C14 glucose amides, C8-C14 alkyl polyglucosides, sucrose cocoate, sucrose laurate, lauramine oxide, cocoamine oxide, and mixtures thereof.

The amount of nonionic surfactant ranges from about 0.1 to about 20 weight percent of the composition. Preferably, the amount of nonionic surfactant ranges from about 1 to about 10 weight percent of the composition.

Amphoteric Surfactants

The term "amphoteric surfactant," as used herein, is also intended to encompass zwitterionic surfactants, which are well known to formulators skilled in the art as a subset of amphoteric surfactants.

A wide variety of amphoteric surfactants can be used. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants are disclosed in McCutcheon's, *Detergents and Emulsifiers*, North American edition (1986), published by Allured Publishing Corporation; and McCutcheon's, *Functional Materials*, North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl)carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl)sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

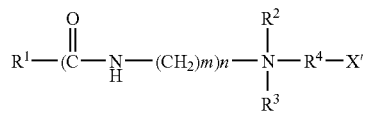

wherein $R_1$ is unsubstituted, saturated or unsaturated, straight or branched chain alkyl having from about 9 to about 22 carbon atoms. Preferred $R_1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R_2$ and $R_3$ are independently selected from the group consisting of alkyl having from 1 to about 3 carbon atoms, unsubstituted or mono-substituted with hydroxy, preferred $R_2$ and $R_3$ are $CH_3$; X is selected from the group consisting of $CO_2$, $SO_3$ and $SO_4$; $R_4$ is selected from the group consisting of saturated or unsaturated, straight or branched chain alkyl, unsubstituted or monosubstituted with hydroxy, having from 1 to about 5 carbon atoms. When X is $CO_2$, $R_4$ preferably has 1 or 3 carbon atoms, more preferably 1 carbon atom. When X is $SO_3$ or $SO_4$, $R_4$ preferably has from about 2 to about 4 carbon atoms, more preferably 3 carbon atoms.

Examples of amphoteric surfactants of the present invention include the following compounds: Cetyl dimethyl betaine (this material also has the CTFA designation cetyl betaine)

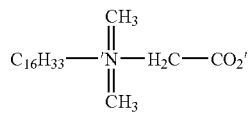

Cocamidopropylbetaine

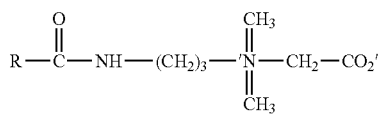

wherein R has from about 9 to about 13 carbon atoms
Cocamidopropyl Hydroxy Sultaine

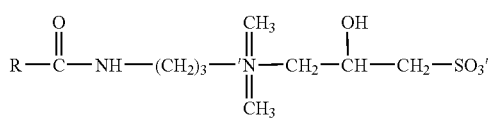

wherein R has from about 9 to about 13 carbon atoms.

Examples of other useful amphoteric surfactants are alkyliminoacetates, and iminodialkanoates and aminoalkanoates of the formulas $RN[CH_2)_mCO_2M]_2$ and $RNH(CH_2)_mCO_2M$ wherein m is from 1 to 4, R is a $C_8$-$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylamino-propane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred amphoteric surfactants are selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

The amount of amphoteric surfactant in the composition may range from about 0.5 to about 20, preferably about 1 to about 10, weight percent of the composition.

Humectant

The composition also contains at least one humectant. The humectant may be selected from a variety of known compounds. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: $HO-(R''O)_b-H$, wherein R'' is an alkylene group having from about 2 to about 3 carbon atoms and b is an integer of from about 2 to about 10; 3) polyethylene glycol ether of methyl glucose of formula $CH_3-C_6H_{10}O_5-(OCH_2CH_2)_c-OH$, wherein c is an integer from about 5 to about 25; 4) urea; and 5) mixtures thereof, with glycerine being the preferred humectant.

The amount of humectant in the composition ranges from about 0.1 to about 50 weight percent. Preferably, the amount of humectant ranges from about 5 to about 15.

Thickener

The composition may optionally contain at least one thickener. The thickener may be selected from a variety of known compounds. Examples of suitable thickeners nonexclusively include: mono or diesters of 1) polyethylene glycol of formula: $HO-(CH2CH2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

The amount of thickener in the composition ranges from about 0.01 to about 20 weight percent. Preferably, the amount of thickener ranges from about 0.1 to about 2 weight percent.

The composition may also contain various preservatives, conditioning agents, fragrances, etc., as known in the art.

Clarity

The composition of the invention is clear. That is, the composition exhibits a light transmittance of at least about 50%, preferably at least about 80% or 95%, most preferably at least about 98%, as measured using a UV spectrophotometer, for example a Model DU Beckman UV spectrophotometer, at a wavelength of 800 nm and utilizing a 1 cm cell.

In one embodiment, substantially all, preferably all of the ingredients of the composition are water soluble. Those ingredients that are not water soluble may be solubilized by the surfactants present in the composition. This provides a particularly clear composition.

Moisturization

The composition advantageously provides excellent moisturization duration. The moisturization duration of the composition is at least 4 hours, preferably at least 12 hours, more preferably at least 24 hours.

Moisturization duration is measured using a corneometer as follows. An area of skin is dried. The composition to be tested is diluted by applying to cotton and soaking with a controlled amount of water. The diluted composition is then applied to the skin and the skin capacitance is measured using the corneometer. The level of moisturisation and its duration are measured versus that for dry skin, which is the control.

Foaming

Despite the excellent moisturization properties of the composition, it also demonstrates good foaming. In general, the amount of foam generated by a cleansing composition is directly related to its perceived efficacy. The greater the volume of foam produced and the greater the stability of the foam, the more efficient the perceived cleansing action.

In particular, the composition provides a foam volume of at least 300 mL, preferably at least about 600 mL, more preferably at least about 800 mL. Foam volume is measured using a SITA Foam Tester using the body wash setting as follows. A stirrer is used to create foam in a temperature-controlled glass vessel containing a pre-determined volume of the composition, which is stirred for a pre-determined time. The foam volume is measured using sensors across the whole surface area. The foam volume measured over time without stirring (foam stability) can also be determined.

Mildness

The composition is also advantageously mild. In one embodiment, the composition is mild to the eyes. As used herein, "mild to the eyes" refers to compositions that possess a relatively high TEP value as determined in accordance with the TEP Test as set forth herein.

In another embodiment, the composition is substantially free of ocular sting. As used herein, "substantially free of ocular sting" or "substantial lack of ocular sting" refers to compositions that possess relatively low sting values as determined in accordance with the Ocular Sting Test as follows.

"Mild to the skin" refers to compositions that have low skin irritancy properties as indicated by: a) a relatively high TEP value as determined in accordance with the TEP Test as follows; and/or b) a passing score in the four screening tests (cell viability; cell lysis; and cytokine release (IL-1∝ and IL-1ra) performed in accordance with the Skin Assay Test as follows.

Trans-Epithelial Permeability Test ("TEP Test"): Irritation to the eyes expected for a given formulation is measured in accordance with the Invittox Protocol Number 86, the "Trans-epithelial Permeability (TEP) Assay" as set forth in Invittox Protocol Number 86 (May 1994). In general, the ocular irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the EC50 (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Skin Assay Test—Mildness is determined using a skin equivalent model as described by Bernhofer, et al., Toxicology in Vitro, 219-229 (1999), which is incorporated by reference herein. This model utilizes sequential screens for determining cell viability, cell lysis and cytokine release in order to evaluate the mildness of a surfactant system to the skin. Cell viability is determined using an alamarBlue™ assay, which is an indicator of metabolic activity. Cell lysis is detected by measuring lactate dehydrogenase (LDH) activity released from the cytosol of damaged cells. Cytokine release (both IL-1∝ and IL-1ra) is measured for those sample sets which do not exhibit loss of cell viability or cell lysis.

In general, an EpiDerm™ Epi-100 human epidermal model is obtained from MatTek Corporation (Ashland, Mass. USA) and maintained according to the manufacturers' instructions. Normal human-derived epidermal keratinocytes (NREK) are then cultured to form a multilayered differentiated model of the epidermis. After a set of NREKs is exposed in triplicate to 100 µl of a topically applied surfactant sample, it is incubated for about 1 hour. After incubation, the set is washed five times, 400 µl per wash, with phosphate buffered saline (PBS), placed onto a fresh assay media, and returned to the incubator for about 24 hours.

Cell viability of the NREKs is determined 24 and 48 hours post treatment with the alamarBlue™ assay (Alamar Biosciences. Sacramento. Calif. USA) in accordance with manufacturers' protocols and a Cytofluor II Fluorescent Plate Reader (PerSeptive Biosystems. Framingham. Mass. USA). Cell lysis is determined colorimetrically using an LDH cytotoxicity detection kit (Boehringer-Mannheim). Cytokine content is measured using human colorimetric ELISA kits for IL-1∝ (ENDOGEN. Cambridge, Mass. USA), interleukin-1 receptor antagonist (IL-1ra, R&D Systems. Minneapolis. Minn., USA), granulocyte~macrophage colony stimulating factor (GM-CSF). interleukin-6 (IL-6), interleukin-8 (IL-8). interleukin-lO (IL-b) and TNF∝ (PerSeptive Diagnostics. Cambridge, Mass. USA).

Ocular Sting Test—Using a double-blinded, randomized, two (2) cell study test design, one (1) drop of a sample (e.g. a 10% dilution of a cleansing composition in water) at a temperature of about 38° C. is instilled into a subject's eye. A new sterile disposable eyedropper is used for each sample and disposed of after being used on only one individual's eye. All installations are performed either by an investigator or by a trained technician.

Within 30 seconds, or as closely as possible following instillation, the subject is asked to grade the perceived stinging sensation to the eye utilizing the following criteria:

Sting

0=Within normal limits

1=Mild, very slight

2=Moderate

3=Severe

After 15 minutes and 60 minutes post-instillation, the subject is again asked to grade the perceived stinging sensation to the eye.

The composition of the present invention is preferably used in personal care products such as shampoos, washes, baths, gels, lotions, creams, and the like. The composition may also be used in conjunction with cleansing implements such as wipes, poufs, sponges, cloths, and the like, or may be impregnated therein. The composition may also be combined with such implements for convenient sale and use in the form of a kit.

The following non-limiting examples further illustrate the invention.

EXAMPLES

The following compositions 1-5 according to the invention were prepared. They were tested for moisturization duration, ocular sting and TEP. The results are shown below.

| Ingredient | 1 | 2 | 3 | 4 | 5 |
|---|---|---|---|---|---|
| Aqua | 58.46 | 58.81 | 63.76 | 61.22 | 58.86 |
| PEG-120 Methyl Glucose Dioleate | 0.4 | 1.2 | 0.4 | | 0.5 |
| PEG-150 Distearate | 1.3 | 1.2 | 0.8 | 2 | 1.3 |
| Sodium Lauryl Ether Sulfate, Aqua | 4.75 | 4.75 | 4.75 | 4.51 | 4.75 |
| Sodium Lauroyl Glutamate, Aqua | 4.94 | | | 4.69 | 4.94 |
| Coco-Glucoside, Aqua | 3.61 | 7.36 | 3.61 | 3.43 | 3.61 |
| Cocamidopropyl Brtaine, Aqua | 7.78 | 7.78 | 7.78 | 7.39 | 7.78 |
| Polysorbate 20 | | | | 0.1 | 0.1 |
| quaternium 80 | 0.5 | 0.5 | 0.5 | | |
| Paraffinum Liquidum | 0.1 | 0.1 | 0.1 | 0.1 | 0.1 |
| PEG 7 glyceryl cocoate | 3.5 | 3.5 | 3.5 | 2 | 3.5 |
| Polyquaternium-10 | 0.1 | 0.1 | 0.1 | | |
| Tocopheryl acetate | 0.5 | 0.5 | 0.5 | 0.5 | 0.5 |
| Allantoin | 0.1 | 0.1 | 0.1 | 0.1 | 0.1 |
| Glycerine | 12 | 12 | 12 | 12 | 12 |
| Sodium Benzoate | 0.5 | 0.5 | 0.5 | | 0.5 |
| Phenoxyethanol | | | | 0.7 | |
| Methylparaben | | | | 0.2 | |
| Propylparaben | | | | 0.15 | |
| Ethylparaben | | | | 0.15 | |
| Tetrasodium EDTA | 0.2 | 0.2 | 0.2 | 0.2 | 0.2 |
| PARFUM | 0.4 | 0.4 | 0.4 | 0.4 | 0.4 |
| Citric Acid | 0.86 | 1 | 1 | 0.16 | 0.86 |
| | | | | | |
| Total | 100 | 100 | 100 | 100 | 100 |
| Ocular Sting | Pass (1) | Pass (0) | | | |
| Moisturization Degree | 24 hours | 24 hours | 24 hours | 24 hours | |
| TEP Test | Pass | Pass | | Pass | Pass |

We claim:

1. A clear cleansing composition comprising 0.05 to 30 weight % of an anionic surfactant selected from the group consisting of sodium lauryl ether sulfate, sodium lauroyl glutamate, and mixtures thereof, 05 to 20 weight % of an amphoteric surfactant selected from the group consisting of disodium lauroamphodiacetate, sodium lauroamphoacetate, cetyl dimethyl betaine, co-coamidopropyl betaine, cocoamidopropyl hydroxyl sultaine, and mixtures thereof, 0.1 to 20 weight % of a non-ionic surfactant selected from the group consisting of $C_8$-$C_{14}$-glucoseamides, $C_8$-$C_{14}$-alkylpolyglucosides, sucrose cocoate, sucrose laurate, lauramine oxide, cocoamine oxide, and mixtures thereof, 0.1 to 50 weight % of a humectant selected from the group consisting of glycerine, PEG-7 glyceryl cocoate and mixtures thereof, and 0.01 to 20 weight % a thickener selected from the group consisting of PEG-150 distearate, PEG-120 methyl glucose dioleate, and mixtures thereof, wherein said composition provides moisturization duration for at least about four hours.

2. A clear cleansing composition comprising 1 to 10 weight % of an anionic surfactant selected from the group consisting of sodium lauryl ether sulfate, sodium lauroyl glutamate, and mixtures thereof, 1 to 10 weight % of an amphoteric surfactant selected from the group consisting of disodium lauroamphodiacetate, sodium lauroamphoacetate, cetyl dimethyl betaine, cocoamidopropyl betaine, cocoamidopropyl hydroxyl sultaine, and mixtures thereof, 1 to 10 weight % of a non-ionic surfactant selected from the group consisting of $C_8$-$C_{14}$-glucoseamides, $C_8$-$C_{14}$-alkylpolyglucosides, sucrose cocoate, sucrose laurate, lauramine oxide, cocoamine oxide, and mixtures thereof, 5 to 50 weight % of a humectant selected from the group consisting of glycerine, PEG-7 glyceryl cocoate, and mixtures thereof, and 0.01 to 2 weight % of a thickener selected from the group consisting of PEG-150 distearate, PEG-120 methyl glucose dioleat, and mixtures thereof.

* * * * *